(12) United States Patent
Leinekugel Le Cocq et al.

(10) Patent No.: US 11,179,655 B2
(45) Date of Patent: Nov. 23, 2021

(54) SIMULATED MOVING BED SEPARATION METHOD AND DEVICE WITH REDUCED NUMBER OF BEDS AND BYPASS FLUID FLOW

(71) Applicant: IFP Energies Nouvelles, Rueil-Malmaison (FR)

(72) Inventors: Damien Leinekugel Le Cocq, Rueil-Malmaison (FR); Gerard Hotier, Rueil-Malmaison (FR); Pierre-Yves Le Goff, Rueil-Malmaison (FR); Fabian Lambert, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 149 days.

(21) Appl. No.: 16/445,544

(22) Filed: Jun. 19, 2019

(65) Prior Publication Data
US 2019/0388802 A1 Dec. 26, 2019

(30) Foreign Application Priority Data
Jun. 20, 2018 (FR) ...................................... 1855448

(51) Int. Cl.
*C07C 7/13* (2006.01)
*B01D 15/18* (2006.01)
*C07C 7/00* (2006.01)

(52) U.S. Cl.
CPC ....... *B01D 15/1835* (2013.01); *B01D 15/185* (2013.01); *C07C 7/005* (2013.01); *C07C 7/13* (2013.01); *B01D 2215/026* (2013.01)

(58) Field of Classification Search
CPC .............. B01D 15/1835; B01D 15/185; B01D 2215/026; B01D 15/1828; B01D 15/1842; C07C 7/005; C07C 7/13; C07C 7/12
See application file for complete search history.

(56) References Cited

U.S. PATENT DOCUMENTS

2010/0048973 A1 * 2/2010 Decoodt .................. C07C 7/13
585/822

* cited by examiner

*Primary Examiner* — Thuan D Dang
(74) *Attorney, Agent, or Firm* — Millen White Zelano & Branigan, PC; Brion P. Heaney

(57) ABSTRACT

Method for the simulated moving bed (SMB) separation of a feedstock (F), in which: at least one zone (1, 2, 3, 4) contains fewer than three beds, if the stream (D, E, F, R) delimiting said zone and situated upstream of said zone is injected or withdrawn at the plate $P_i$ via the bypass line $L_{i/i+1}$, then the stream delimiting said zone and situated downstream of said zone is injected/withdrawn at the plate $P_j$ via the bypass line $L_{j/j+1}$, and if the stream delimiting said zone and situated downstream of said zone is injected or withdrawn at the plate $P_i$ via the bypass line $L_{i-1/i}$, then the stream delimiting said zone and situated upstream of said zone is injected/withdrawn at the plate $P_j$ via the bypass line $L_{j-1/j}$.

20 Claims, 5 Drawing Sheets

SIMULATED MOVING BED SEPARATION METHOD AND DEVICE WITH REDUCED NUMBER OF BEDS AND BYPASS FLUID FLOW

TECHNICAL FIELD

The invention relates to the field of the separation of natural or chemical products that are difficult to separate by distillation. Use is then made of a family of methods, and of associated devices, known by the name of simulated moving bed separation methods or devices, using either simulated countercurrent flow or simulated concurrent flow, and that will be referred to hereinafter by the abbreviation "SMB".

The fields concerned are, notably and not exclusively:
the separation of, on the one hand, normal paraffins from, on the other hand, branched paraffins, naphthenes and aromatics;
olefin/paraffin separation;
separation of paraxylene from other C8 aromatic isomers;
separation of metaxylene from other C8 aromatic isomers; and
separation of ethylbenzene from other C8 aromatic isomers.

Outside of refinery and petrochemical complexes, there are numerous other applications including glucose/fructose separation, the separation of cresol position isomers, optical isomers, etc.

PRIOR ART

SMB separation is well known in the prior art. As a general rule, a column using simulated moving bed technology comprises at least three zones, and possibly four or five, each of these zones being made up of a certain number of successive beds, and each zone being defined by its position between a feed point and a withdrawal point. Typically, an SMB column is fed with at least one feedstock that is to be fractionated and with a desorbent (sometimes referred to as an eluent), and at least one raffinate and an extract are withdrawn from said column.

The feed and withdrawal points are modified over the course of time, typically shifted in the same direction by an amount corresponding to one bed.

By definition, each of the operating zones is designated by a number:
zone 1=zone for the desorption of the compounds from the extract, this zone being comprised between the injection of the desorbent and the tapping-off of the extract;
zone 2=zone for the desorption of the compounds from the raffinate, this zone being comprised between the tapping-off of the extract and the injection of the feedstock that is to be fractionated;
zone 3=zone for the adsorption of the compounds from the extract, this zone being comprised between the injection of the feedstock and the withdrawal of the raffinate; and optionally a zone 4 situated between the withdrawal of the raffinate and the injection of the desorbent.

The state-of-the-art describes in depth the various devices and methods that make it possible to achieve the separation of feedstocks in a simulated moving bed.

Particular mention may be made of U.S. Pat. Nos. 2,985,589, 3,214,247, 3,268,605, 3,592,612, 4,614,204, 4,378,292, 5,200,075, 5,316,821. These patents also describe in detail the operation of an SMB device.

SMB devices typically comprise at least one column (and often two), divided into a plurality of successive beds of adsorbent, said beds being separated by plates.

The controlled fluid distribution and extraction means of an SMB device typically employ one of the following two broad types of technology:
Either, for each plate, a plurality of controlled on/off valves for feeding or withdrawing the fluids, these valves typically being situated in the immediate vicinity of the corresponding plate. Each plate typically comprises at least four two-way valves, controlled on an on/off basis, in order respectively to feed the feedstock and the desorbent and withdraw the extract and the raffinate;
or a multi-way rotary valve for feeding or withdrawing fluids across all of the plates.

The present invention notably falls within the context of SMB devices that employ a plurality of valves for feeding and withdrawing the various fluids.

Each of the plates typically comprises a plurality of distribution—mixing—extraction panels, referred to as "DME plates" fed by distribution/extraction lines or systems. The plates may be of any type and of any geometry. They are generally divided into panels, corresponding to adjacent sectors of the cross section of the column, for example panels with angular sectors, as disclosed in U.S. Pat. No. 6,537,451 FIG. 8, or panels with parallel sectors as cut from a circumference, as described in U.S. Pat. No. 6,797,175.

Distribution across each of the beds requires collection of the main stream coming from the previous bed, the possibility of injecting an auxiliary fluid or secondary fluid while at the same time mixing these two fluids as well as possible, or else the possibility of tapping off part of the collected fluid, extracting it in order to send it out of the device and also of redistributing a fluid across the next bed.

One generic problem with all SMB devices is that of minimizing the contamination generated by the liquid lying in the various zones of the circuit or circuits feeding fluids to and withdrawing fluids from the plates, when the feed and withdrawal points are modified during the course of operation of the SMB device.

Specifically, when, during the course of the operating sequence, a line, chamber or zone for the feeding of a plate is no longer swept with a process fluid, it becomes a dead zone in which the liquid stagnates, and is not set back in motion again until another process fluid circulates through it again. Because of the way in which the SMB device operates, this is then a process fluid that generally differs from the fluid that has stagnated in the line concerned.

The mixing, or short-term circulation, of fluids with notably different compositions introduces disturbances into the concentration profile in the zone concerned in comparison with the ideal operation, for which discontinuities in composition are to be avoided.

Another problem lies in the potential recirculations between different zones of the one same plate, and more generally of the entire distribution/extraction system of the one same plate, as a result of very small differences in pressure between the various zones of the plate, something which still introduces disturbances in comparison with the ideal operation.

In order to address these problems associated with recirculations and dead zones, there are various techniques known in the prior art.

Flushing the distribution/extraction system of a given plate with relatively pure desorbent or desired product has already been proposed. This technique does actually make it possible to avoid the desired product being contaminated at the time of its extraction. However, because the flushing liquid has a composition that differs greatly from the liquid it is displacing, this introduces discontinuities in composition which are detrimental to the ideal operation. This first flushing variant typically performs short-term flushing with high concentration gradient. These flushing operations are short in term specifically in order to limit the effects of the discontinuities in composition.

Another solution, as described in U.S. Pat. Nos. 5,972,224 and 6,110,364, is to cause the majority of the main stream to pass towards the inside of the column and a minority of this stream (typically from 1% to 20% of the main stream) to pass towards the outside via external bypass lines running between successive plates. This flushing of the distribution/extraction system at the level of a plate using a stream taken from the plate above is typically performed continuously, so that the lines and zones of the distribution/extraction system are no longer "dead" but constantly flushed.

Such a system with continuous flushing via bypass lines is disclosed in FIG. 2 of patent FR 2,772,634. The bypass lines are generally small in diameter and comprise a small-diameter valve, thereby reducing the cost of the system.

According to the teaching of U.S. Pat. Nos. 5,972,224 and 6,110,364, the desired outcome is for the distribution/extraction system of a given plate to be flushed with liquid that has a composition very similar to that of the liquid displaced (liquid present in the distribution system, or circulating at the level of the plate). In this way, the mixing of fluids of different compositions is minimized and the discontinuities in composition are reduced.

To this end, U.S. Pat. Nos. 5,972,224 and 6,110,364 recommend implementing flushing flow rates in the bypasses such that the rate of passage through each bypass is substantially the same as the rate at which the concentration gradient in the main stream of the SMB device advances. The flushing is then said to be "synchronous" or "at synchronous flow rate". Thus, the various lines and volumes are flushed with a fluid that has a composition substantially identical to that of the liquid found therein, and the liquid circulating through a bypass is reintroduced at a point at which the composition of the main stream is substantially identical.

Patent FR 2,935,100 shows that it is possible to improve the performance of the method by regulating the flow rates in the bypass lines in a given operating zone according to whether or not at least one closed bypass line is present in said zone.

The aforementioned methods make it possible to achieve the objective of commercial purity for a unit comprising a high number of beds. However, the Applicant Company has been able to demonstrate that when considering a simulated moving bed separation unit having a reduced number of beds, e.g. having at least one zone comprising on average fewer than three beds, the "synchronous flushing" teachings of U.S. Pat. Nos. 5,972,224, 6,110,364 and FR 2,935,100 are not enough to obtain commercial purity with a high yield (in excess of 97%).

SUMMARY

In the above-mentioned context, a first object of the present description is to provide an SMB separation method using a low number of beds and making it possible, for equivalent yield, to extract a solute from the feedstock with a higher purity. Specifically, when use is made of an SMB device comprising at least one zone comprising on average fewer than three beds, the Applicant Company has been able to identify, surprisingly, a restricted number of modes of operation of the bypass lines and of the injection and withdrawing lines that make it possible to achieve a commercial level of purity with high yield. A second object is to provide a method that makes it possible, for equivalent purity, to extract a solute from the feedstock with a higher yield.

According to a first aspect, the aforementioned objects, together with other advantages, are obtained by a method for the simulated moving bed separation of a feedstock in a simulated moving bed separation device, the device comprising:
  at least one column comprising a plurality of beds of adsorbent which are separated by plates each comprising a distribution/extraction system; and
  external bypass lines directly joining two successive plates, each external bypass line comprising fluid feed points and effluent withdrawal points, in which method:
  at least one column is fed with the feedstock and a desorbent and at least one extract and at least one raffinate is withdrawn from the at least one column, the feed and withdrawal points being shifted during the course of time by an amount corresponding to one adsorbent bed with a switchover period and determining a plurality of operating zones of the device, and notably the following main zones:
  a zone 1 for the desorption of the compounds from the extract, this zone being comprised between the feed for the desorbent and the withdrawal of the extract,
  a zone 2 for the desorption of the compounds from the raffinate, this zone being comprised between the withdrawal of the extract and the feed for the feedstock,
  a zone 3 for the adsorption of the compounds from the extract, this zone being comprised between the feed for the feedstock and the withdrawal of the raffinate, and
  a zone 4 situated between the withdrawal of the raffinate and the feed for the desorbent;

in which method:
  if a zone contains fewer than 3 beds,
  then, if the stream delimiting the zone concerned and situated upstream of said zone is injected or withdrawn at the plate $P_i$ via the bypass line $L_{i/i+1}$, then the stream delimiting the zone and situated downstream of said zone is injected/withdrawn at the plate $P_j$ via the bypass line $L_{j/j+1}$, and
  if the stream delimiting the zone concerned and situated downstream of said zone is injected or withdrawn at the plate $P_i$ via the bypass line $L_{i-1/i}$, then the stream delimiting the zone and situated upstream of said zone is injected/withdrawn at the plate $P_j$ via the bypass line $L_{j-1/j}$,
  the plate $P_i$ corresponding to one plate of the column,
  the plate $P_j$ corresponding to a plate other than $P_i$,
  the bypass line $L_{i-1/i}$ being the line joining the two successive plates $P_{i-1}$ and $P_i$,
  the bypass line $L_{i/i+1}$ being the line joining the two successive plates $P_i$ and $P_{i+1}$,
  the bypass line $L_{j-1/j}$ being the line joining the two successive plates $P_{j-1}$ and $P_j$,
  the bypass line $L_{j/j+1}$ being the line joining the two successive plates $P_j$ and $P_{j+1}$.

According to one or more embodiments, if zone 1 contains on average fewer than three beds, then when the desorbent is injected on the plate $P_i$ via the bypass line $L_{i/i+1}$, the extract is withdrawn on the plate $P_j$ via the bypass line $L_{j/j+1}$;

if zone 2 contains on average fewer than three beds, then when the feedstock is injected on the plate $P_i$ via the bypass line $L_{i-1/i}$, the extract is withdrawn on the plate $P_j$ via the bypass line $L_{j-1/j}$;
  if zone 3 contains on average fewer than three beds, then when the feedstock is injected on the plate $P_i$ via the bypass line $L_{i/i+1}$, the raffinate is withdrawn on the plate $P_j$ via the bypass line $L_{j/j+1}$; and
  if zone 4 contains on average fewer than three beds, then when the desorbent is injected on the plate $P_i$ via the bypass line $L_{i-1/i}$, the raffinate is withdrawn on the plate $P_j$ via the bypass line $L_{j-1/j}$.

According to one or more embodiments, if zone 1 contains on average fewer than three beds, then when the extract is withdrawn on the plate $P_i$ via the bypass line $L_{i-1/i}$, the desorbent is injected on the plate $P_j$ via the bypass line $L_{j-1/j}$;
  if zone 2 contains on average fewer than three beds, then when the extract is withdrawn on the plate $P_i$ via the bypass line $L_{i/i+1}$, the feedstock is injected on the plate $P_j$ via the bypass line $L_{j/j+1}$;
  if zone 3 contains on average fewer than three beds, then when the raffinate is withdrawn on the plate $P_i$ via the bypass line $L_{i-1/i}$, the feedstock is injected on the plate $P_j$ via the bypass line $L_{j-1/j}$; and
if zone 4 contains on average fewer than three beds, then when the raffinate is withdrawn on the plate $P_i$ via the bypass line $L_{i/i+1}$, the desorbent is injected on the plate $P_j$ via the bypass line $L_{j/j+1}$.

According to one or more embodiments, the plate $P_i$ is connected to the bypass line $L_{i-1/i}$ and to the bypass line $L_{i/i+1}$.

According to one or more embodiments, each plate comprises a plurality of distribution—mixing—extraction panels of the parallel sectors type with asymmetric feed.

According to one or more embodiments, the feedstock contains paraxylene or metaxylene within a mixture of C8 aromatic hydrocarbons.

Embodiments according to the first aspect, together with other features and advantages of the methods according to the first aspect, will become apparent on reading the description which will follow, given solely by way of illustration and without limitation, and with reference to the following drawings.

DETAILED DESCRIPTION

The purpose of the invention is to improve the performance of a simulated bed separation method in comparison with the teachings of U.S. Pat. Nos. 5,972,224, 6,110,364 and FR 2,935,100, when use is made of an SMB device comprising at least one zone comprising on average fewer than three beds.

Figure 1:
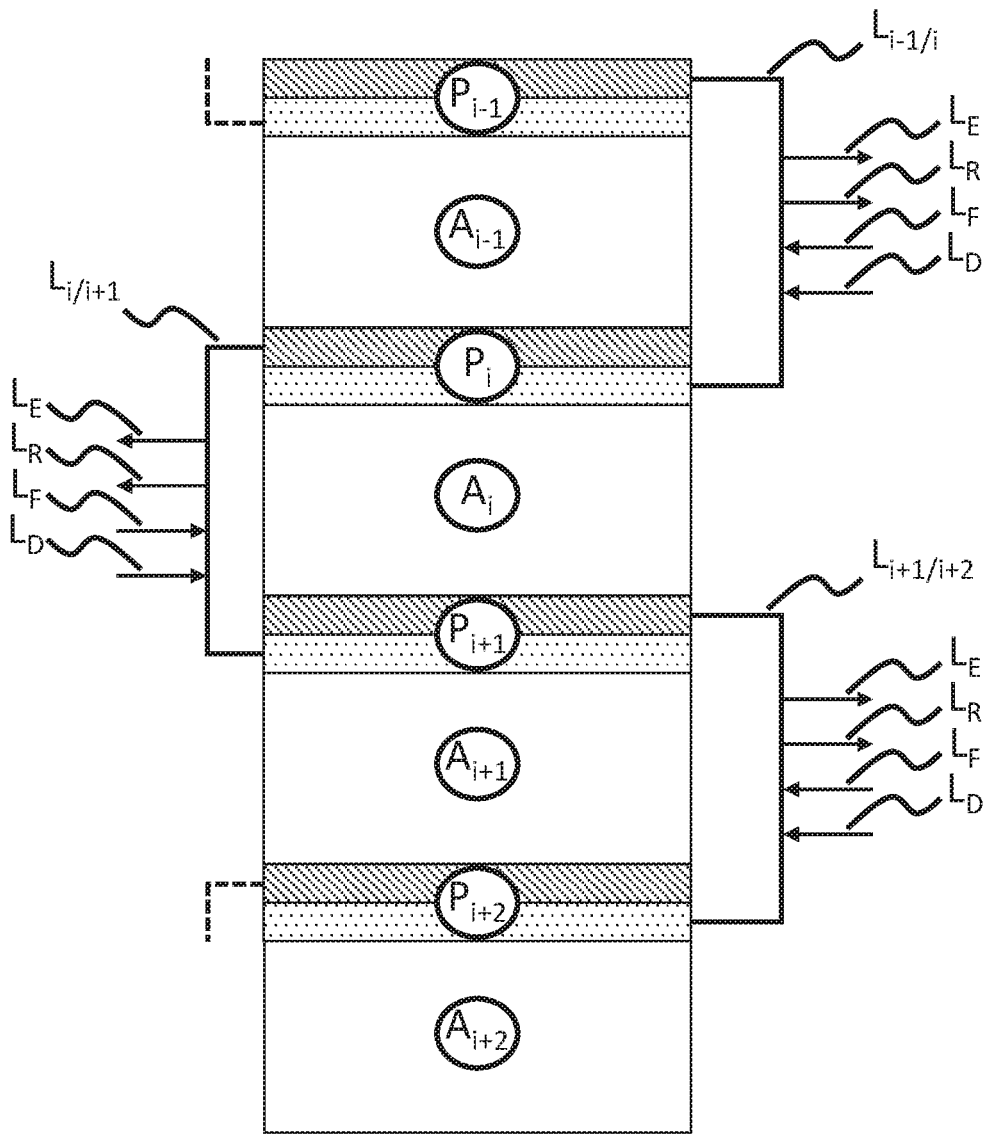
FIG. 1 depicts an SMB device used in the method according to embodiments of the present description, the device comprising a column having a succession of plates ($P_{i-1}$, $P_i$, $P_{i+1}$, $P_{i+2}$) and of beds ($A_{i-1}$, $A_i$, $A_{i+1}$, $A_{i+2}$), and external bypass lines ($L_{i-1/i}$, $L_{i/i+1}$, $L_{i+1/i+2}$).

With reference to FIG. 1, in order to achieve high separation performance using SMB technology with a limited number of beds, the invention proposes a method for the SMB separation of a feedstock F in an SMB device possessing at least one column, said column being made up of a plurality of beds of adsorbent $A_i$, separated by plates $P_i$ each comprising a distribution/extraction system. The SMB device further comprises external bypass lines $L_{i/i+1}$ directly joining two successive plates $P_i$, $P_{i+1}$, notably allowing said plates to be flushed. It being possible for each of these bypass lines $L_{i/i+1}$ to comprise automated means for regulating the flushing flow rate.

According to one or more embodiments, the column comprises n adsorbent beds $A_i$. According to one or more embodiments, n is a natural whole number comprised between 6 and 15, preferably between 8 and 12, i being a natural whole number comprised between 1 and n.

The SMB separation method comprises the following steps: the feedstock F and a desorbent D are fed, and at least one extract E and at least one raffinate R are withdrawn, the feed and withdrawal points being shifted over the course of time by an amount corresponding to one adsorbent bed, with a changeover period (period denoted ST between two successive feed/withdrawal changeovers) and determining a plurality of operating zones of the SMB device, and notably the following main zones:

a zone 1 for the desorption of the compounds from the extract, this zone being comprised between the feed for the desorbent D and the withdrawal of the extract E;

a zone 2 for the desorption of the compounds from the raffinate, this zone being comprised between the withdrawal of the extract E and the feed for the feedstock F;

a zone 3 for the adsorption of the compounds from the extract, this zone being comprised between the feed for the feedstock and the withdrawal of the raffinate R; and a zone 4 situated between the withdrawal of the raffinate R and the feed for the desorbent D.

It should be noted that an external bypass line $L_{i/i+1}$ directly joining two successive plates $P_i$, $P_{i+1}$, is said to belong to a zone when the bed $A_i$ situated between the plates $P_i$ and $P_{i+1}$ belongs to said zone. In addition, the n adsorbent beds $A_i$ are distributed between zones 1 to 4 in configurations referred to as being of type a/b/c/d, which means to say that the distribution of the beds is as follows:

a is the mean number of beds in zone 1;
b is the mean number of beds in zone 2;
c is the mean number of beds in zone 3; and
d is the mean number of beds in zone 4.

In the present description, a zone comprising "on average" fewer than three beds corresponds to a zone which may, at isolated points, comprise more than two beds for part of the changeover period ST (e.g. when the changeovers of the injection points and of the withdrawal points are not in phase), but in which the average number of beds per changeover period ST is strictly lower than three.

According to one or more embodiments:
a=(n*0.208)*(1±0.2);
b=(n*0.375)*(1±0.2);
c=(n*0.292)*(1±0.2);
d=(n*0.125)*(1±0.2).

When a fluid (feedstock F or desorbent D) is injected or when a fluid (extract E or raffinate R) is withdrawn at a plate $P_i$, use is made of the corresponding injection line $L_F$ or $L_D$ or withdrawal line $L_E$ or $L_R$ which is connected to one of the two bypass lines ($L_{i-1/i}$ or $L_{i/i+1}$) connected to the plate $P_i$.

The method according to the invention is characterized in that it respects the following rules:

A/ if a zone contains fewer than 3 beds,
then, if the stream delimiting the zone concerned and situated upstream of said zone is injected or withdrawn at the plate $P_i$ via the bypass line $L_{i/i+1}$, then the stream delimiting the zone and situated downstream of said zone is injected/withdrawn at the plate $P_j$ via the bypass line $L_{j/j+1}$, and B/ if the stream delimiting the zone concerned and situated downstream of said zone is injected or withdrawn at the plate $P_i$ via the bypass line $L_{i-1/i}$, then the stream delimiting the zone and situated upstream of said zone is injected/withdrawn at the plate $P_j$ via the bypass line $L_{j-1/j}$, the plate $P_i$ corresponding to one plate of the column,
the plate $P_j$ corresponding to a plate other than $P_i$,
the bypass line $L_{i-1/i}$ being the line joining the two successive plates $P_{i-1}$ and $P_i$,
the bypass line $L_{i/i+1}$ being the line joining the two successive plates $P_i$ and $P_{i+1}$,
the bypass line $L_{j-1/j}$ being the line joining the two successive plates $P_{j-1}$ and $P_j$,
the bypass line $L_{j/j+1}$ being the line joining the two successive plates $P_j$ and $P_{j+1}$.

j is a natural whole number comprised between 1 and n and different from i.

if a zone contains more than 3 beds, then it is possible to inject or withdraw via the bypass line $L_{i/i+1}$ or the bypass line $L_{i-1/i}$, provided that rules A/ and B/ are respected.

j is a natural whole number comprised between 1 and n and different from i.

Figure 2:
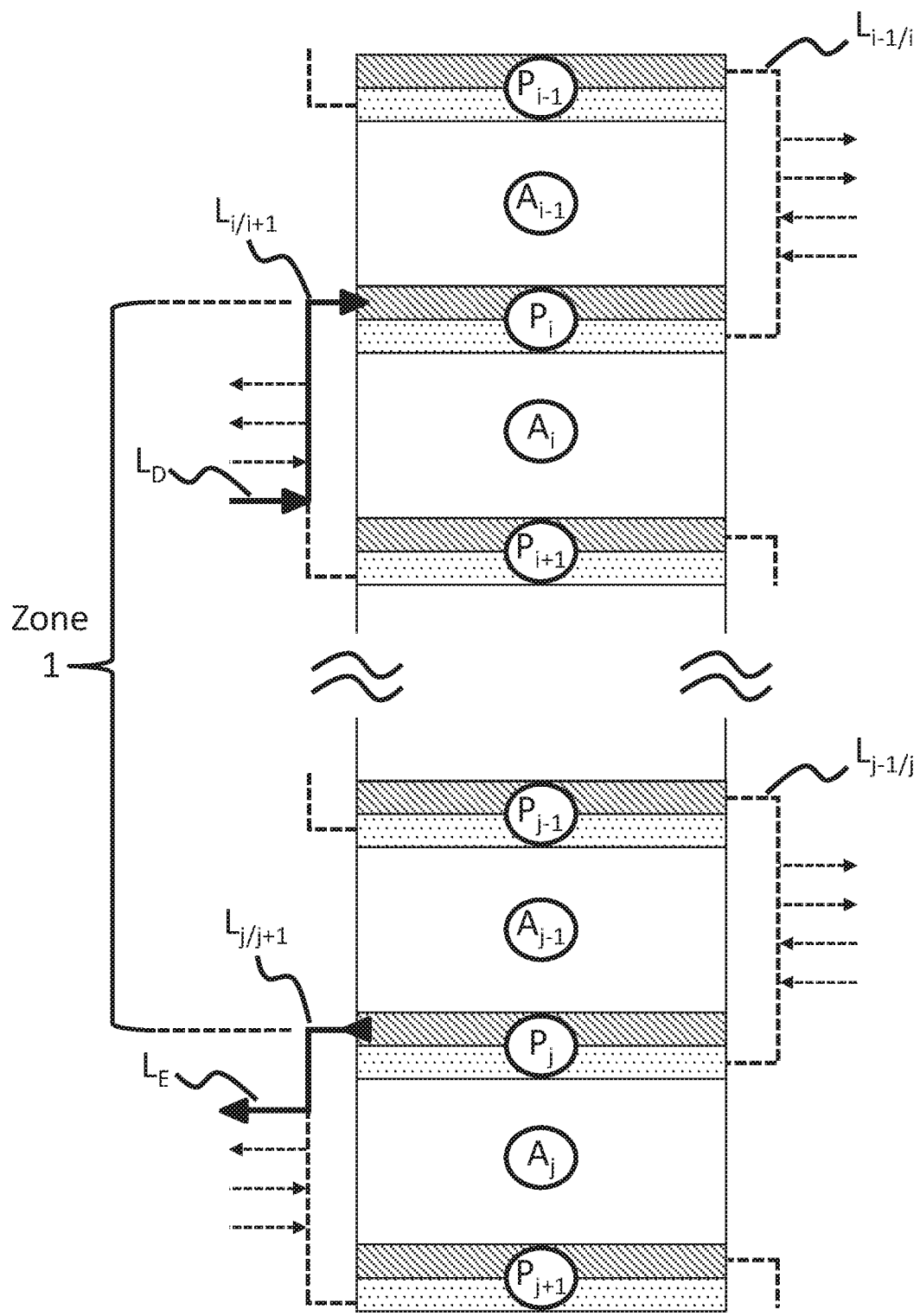
FIG. 2 depicts an SMB device used in the method according to embodiments of the present description, the device being in a mode of operation in which zone 1 for the desorption of the compounds from the extract is comprised between the desorbent feed at plate $P_i$ and the extract withdrawal at plate $P_j$.

According to one or more embodiments, if zone 1 contains on average fewer than three beds, then when the desorbent is injected on the plate $P_i$ via the bypass line $L_{i/i+1}$, the extract is withdrawn on the plate $P_j$ via the bypass line $L_{j/j+1}$. For example, with reference to FIG. 2, if zone 1 contains on average fewer than three beds, then if the desorbent is injected on the plate $P_i$ via the bypass line $L_{i/i+1}$, then the extract must be withdrawn on the plate $P_j$ via the bypass line $L_{j/j+1}$.

Figure 3:
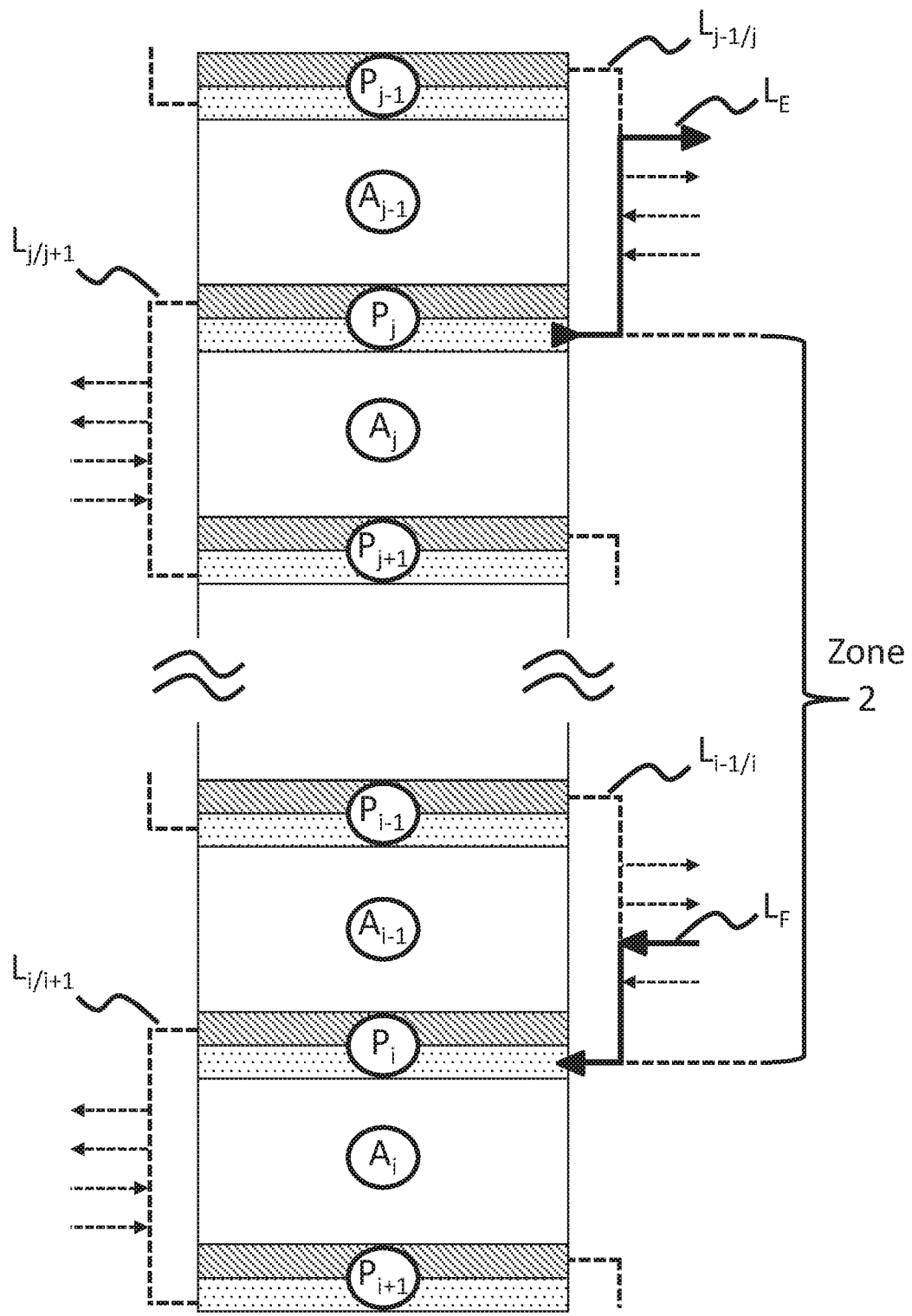
FIG. 3 depicts an SMB device used in the method according to embodiments of the present description, the device being in a mode of operation in which zone 2 for the desorption of the compounds from the raffinate is comprised between the extract withdrawal at plate $P_j$ and the feedstock F feed at plate $P_i$.

According to one or more embodiments, if zone 2 contains on average fewer than three beds, then when the feedstock is injected on the plate $P_i$ via the bypass line $L_{i-1/i}$, the extract is withdrawn on the plate $P_j$ via the bypass line $L_{j-1/j}$. For example, with reference to FIG. 3, if zone 2 contains on average fewer than three beds, then if the feedstock is injected on the plate $P_i$ via the bypass line $L_{i-1/i}$, then the extract must be withdrawn on the plate $P_j$ via the bypass line $L_{j-1/j}$.

Figure 4:
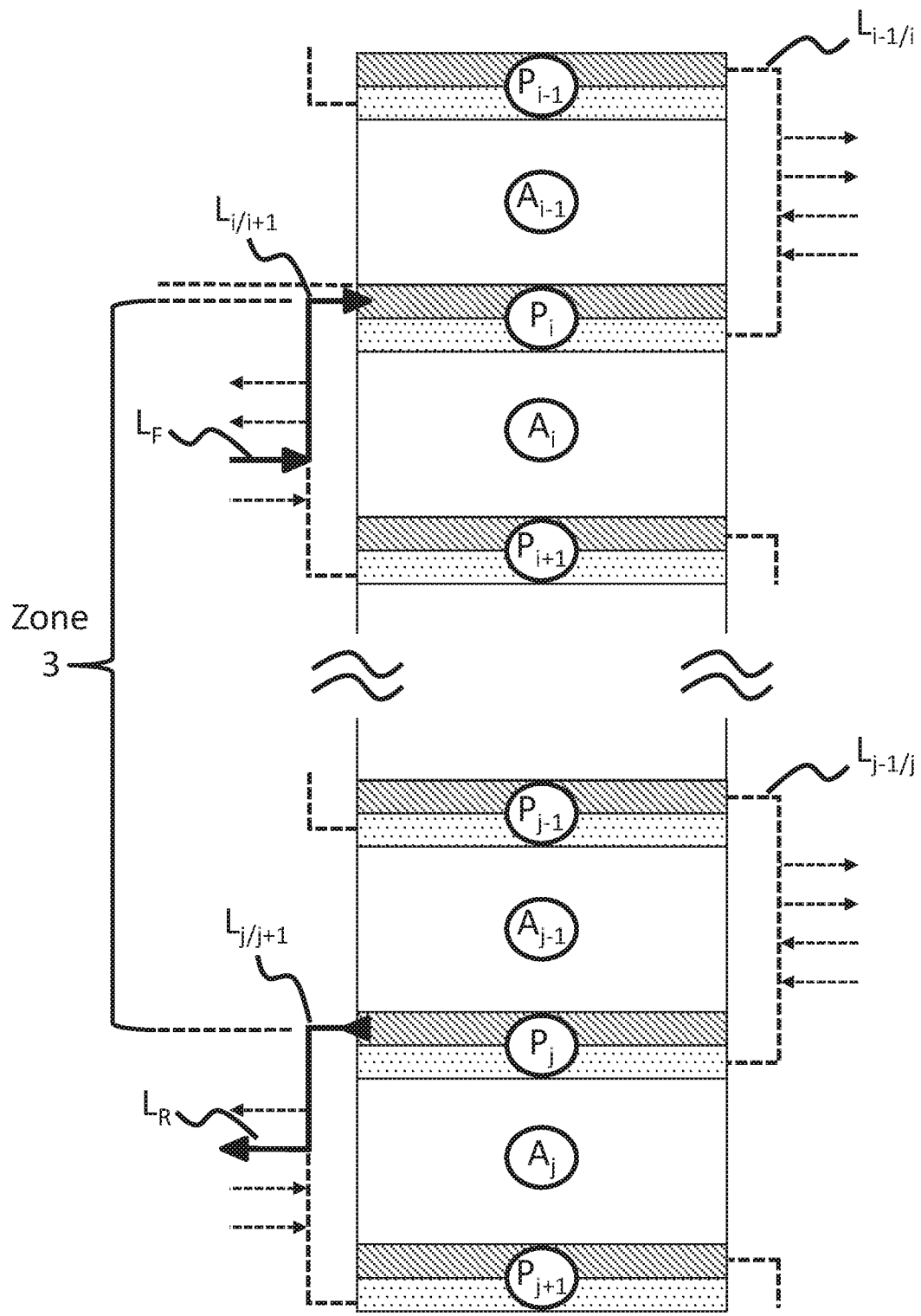
FIG. 4 depicts an SMB device used in the method according to embodiments of the present description, the device being in a mode of operation in which zone 3 for the absorption of the compounds from the extract is comprised between the feedstock feed at plate $P_i$ and the raffinate withdrawal at plate $P_j$.

According to one or more embodiments, if zone 3 contains on average fewer than three beds, then when the feedstock is injected on the plate $P_i$ via the bypass line $L_{i/i+1}$, the raffinate is withdrawn on the plate $P_j$ via the bypass line $L_{j/j+1}$. For example, with reference to FIG. 4, if zone 3 contains on average fewer than three beds, then if the feedstock is injected on the plate $P_i$ via the bypass line $L_{i/i+1}$ then the raffinate must be withdrawn on the plate $P_j$ via the bypass line $L_{j/j+1}$.

Figure 5:
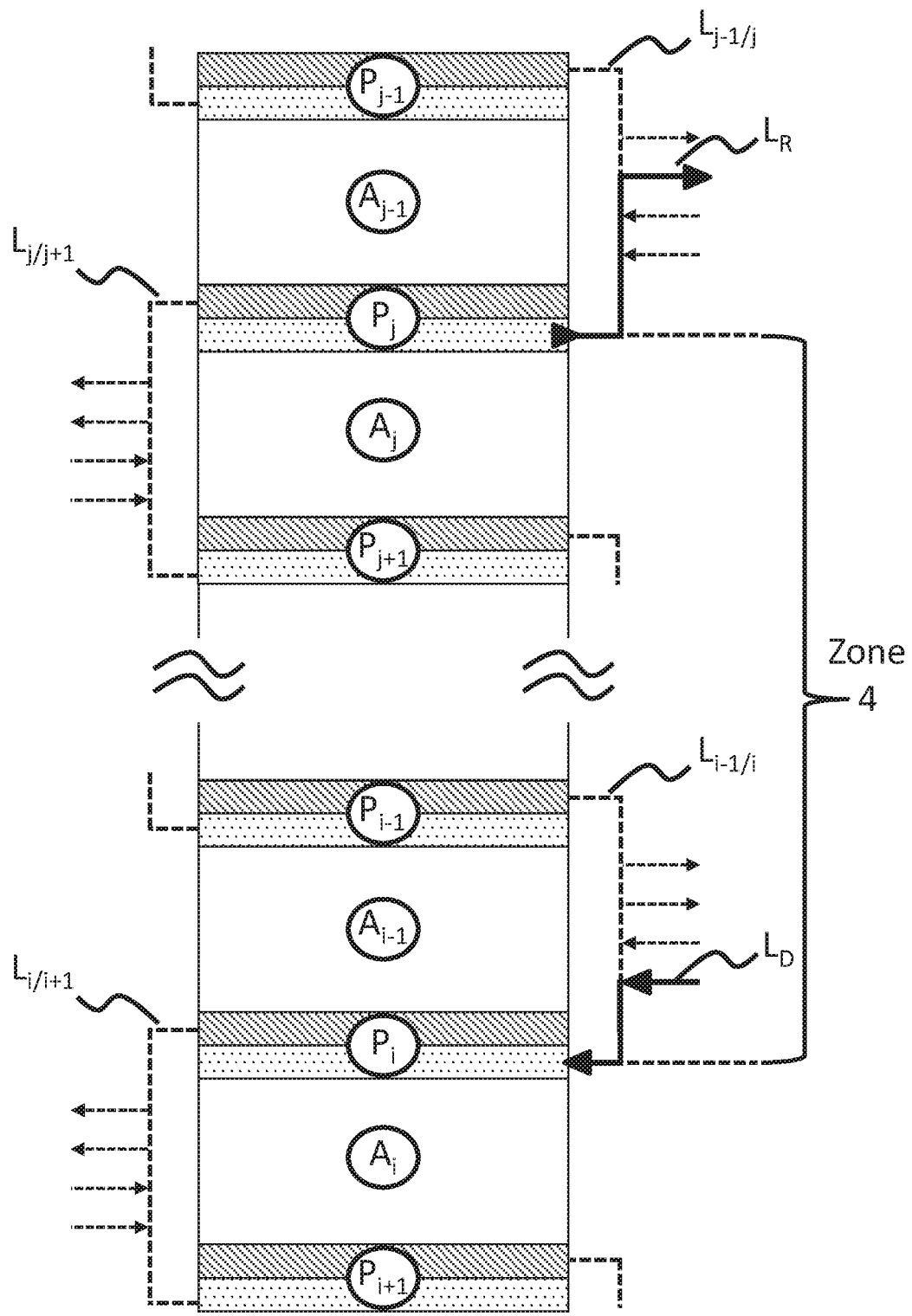
FIG. 5 depicts an SMB device used in the method according to embodiments of the present description, the device being in a mode of operation in which zone 4 is comprised between the raffinate withdrawal at plate $P_j$ and the desorbent feed at plate $P_i$.

According to one or more embodiments, if zone 4 contains on average fewer than three beds, then when the desorbent is injected on the plate $P_i$ via the bypass line $L_{i-1/i}$, the raffinate is withdrawn on the plate $P_j$ via the bypass line $L_{j-1/j}$. For example, with reference to FIG. 5, if zone 4 contains on average fewer than three beds, then if the desorbent is injected on the plate $P_i$ via the bypass line $L_{i-1/i}$, then the raffinate must be withdrawn on the plate $P_j$ via the bypass line $L_{j-1/j}$.

According to one or more embodiments, if zone 1 contains on average fewer than three beds, then when the extract is withdrawn on the plate $P_i$ via the bypass line $L_{i-1/i}$, the desorbent is injected on the plate $P_j$ via the bypass line $L_{j-1/j}$.

According to one or more embodiments, if zone 2 contains on average fewer than three beds, then when the extract is withdrawn on the plate $P_i$ via the bypass line $L_{i/i+1}$, the feedstock is injected on the plate $P_j$ via the bypass line $L_{j/j+1}$.

According to one or more embodiments, if zone 3 contains on average fewer than three beds, then when the raffinate is withdrawn on the plate $P_i$ via the bypass line $L_{i-1/i}$, the feedstock is injected on the plate $P_j$ via the bypass line $L_{j-1/j}$.

According to one or more embodiments, if zone 4 contains on average fewer than three beds, then when the raffinate is withdrawn on the plate $P_i$ via the bypass line $L_{i/i+1}$, the desorbent is injected on the plate $P_j$ via the bypass line $L_{j/j+1}$.

Each plate $P_i$ comprises two chambers for accomplishing the sequential operations of feeding the feedstock F or injecting the desorbent D and extracting the raffinate R or the extract E. The present invention relates to columns having two chambers per plate $P_i$. There are a number of possible solutions for using the two chambers, each one of them being able to be used for the injection or the withdrawal of one or more streams. According to one or more embodiments, a first chamber performs the operations of injecting feedstock F or desorbent D, and the other chamber performs the operations of withdrawing raffinate R or extract E. According to one or more embodiments, one chamber is used for injecting the feedstock F and withdrawing the raffinate R, the other handling the injection of desorbent D and the withdrawal of the extract E. The above examples are nonlimiting, other uses of the two chambers being possible. Each bed i is equipped with a bypass line which connects one chamber of the upstream plate to one chamber of the downstream plate.

According to one or more embodiments, the feedstock is selected from the group consisting of a mixture of essentially C8 aromatic compounds (e.g. xylenes and ethylbenzene). According to one or more embodiments, the mixture comprises at least 95%, preferably at least 97% (e.g. at least 99%) of essentially C8 aromatic compounds.

The method according to the present invention more particularly applies to the separation of a feedstock containing paraxylene and/or metaxylene within a mixture of C8 aromatic hydrocarbons. According to one or more embodiments, the feedstock comprises at least 15 wt % of paraxylene and/or 30 wt % of metaxylene with respect to the total weight of the feedstock.

One example of an SMB separation method of great industrial importance is the separation of C8 aromatic fractions in order to produce paraxylene of commercial purity, typically at a purity of at least 99.7 wt %, and a raffinate rich in ethylbenzene, orthoxylene and metaxylene.

According to one or more embodiments, the adsorbent is selected from the group made up of zeolites of the faujasite type, of type NaY, BaX, BaKX, BaLSX. For preference, the adsorbent is selected from the group made up of BaX, BaKX, NaY.

According to one or more embodiments, the desorbent is selected from the group made up of one or more isomers of diethylbenzene and toluene. For preference, the desorbent is selected from the group made up of paradiethylbenzene and toluene.

According to one or more embodiments, the temperature of the column is comprised between 120° C. and 190° C. For preference, the temperature of the column is comprised between 150° C. and 180° C.

According to one or more embodiments, the pressure in the column is comprised between 0.3 MPa and 3 MPa. According to one or more embodiments, the pressure in the column is comprised between 0.5 MPa and 3 MPa. According to one or more embodiments, the pressure in the column is comprised between 0.8 MPa and 3 MPa. For preference, the pressure in the column is comprised between 1 MPa and 2 MPa.

According to one or more embodiments, the changeover period ST used is comprised between 20 seconds and 120 seconds. For preference, the changeover period ST used is comprised between 40 seconds and 100 seconds.

Of course, these application examples are entirely non-limiting, and other applications are possible, notably in the field of the separation of normal and iso paraffins or normal and iso olefins.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1855448, filed Jun. 20, 2018 are incorporated by reference herein.

EXAMPLES

The invention will be better understood from reading the following examples.

Example 1

Reference Method

Consider an SMB unit made up of 12 beds, of length 1.3 m and of internal radius 3.5 m, with an injection of feedstock $L_F$, an injection of desorbent $L_D$ (which may also be referred to as eluent or solvent), a withdrawal of extract $L_E$ and a withdrawal of raffinate $L_R$.

The adsorbent used is a zeolite of type BaX, and the eluent is paradiethylbenzene. The temperature is 175° C., and the pressure is 15 bar.

The feedstock is made up of 23 wt % of paraxylene, of 22 wt % of orthoxylene, of 50 wt % of metaxylene, and of 5 wt % of ethylbenzene with respect to the total weight of the feedstock. The changeover period ST employed is 45 seconds.

The feedstock and desorbent injection liquid flow rates are as follows:
565 $m^3 \cdot h^{-1}$ for the feedstock;
710 $m^3 \cdot h^{-1}$ for the desorbent;
namely a solvent ratio S/F=1.3.

The beds are distributed in the 2/5/3/2 configuration, which means to say that the distribution of the beds is as follows:
2 beds in zone 1;
5 beds in zone 2;
3 beds in zone 3;
2 beds in zone 4.

The plates have two mixing chambers. The total volume $(V_i+V_{i+1}+V_{i/i+1})$, where $VL_{i/i+1}$ is the volume of the bypass line from plate $P_i$ to plate $P_{i+1}$ and where $V_i$ is the volume of the distribution/extraction system for plate $P_i$, represents 3% of the volume of the bed comprised between plate $P_i$ and plate $P_{i+1}$.

The synchronism is set at 100% for all the open bypass lines.

Reference Method

The effluent (raffinate or extract) withdrawal lines are situated downstream of the bypass line isolation valve (referred to more simply as "downstream of the bypass line valve").

The feed lines (feeding feedstock or desorbent) are situated upstream of the isolation valve.

When a fluid (feedstock or desorbent) is injected at plate $P_i$, use is made of an injection line connected to the bypass line $L_{i/i+1}$. The isolation valve isolating the bypass line $L_{i/i+1}$ is then closed to ensure that the injected fluid does indeed flow towards the plate $P_i$.

When an effluent (extract or raffinate) is withdrawn at plate $P_i$, use is made of a withdrawal line connected to the bypass line $L_{i-1/i}$. The isolation valve isolating the bypass line $L_{i-1/i}$ is then closed.

In order to gain a clear understanding of the configuration of the reference method, a description is given of the configuration of the method when the desorbent is injected at plate $P_1$. At that moment, the desorbent is injected via the bypass line $L_{1/2}$. The feedstock is then injected at plate $P_8$ via the bypass line $L_{8/9}$. The extract is withdrawn at plate $P_3$ via the bypass line $L_{2/3}$. The raffinate is withdrawn at plate $P_{11}$ via the bypass line $L_{10/11}$.

In the reference method, zone 1 contains fewer than 3 beds. When the desorbent is injected at plate $P_i$ via the bypass line $L_{i/i+1}$, the extract is withdrawn at plate $P_j$ (i.e., $P_{i+2}$) via the bypass line $L_{j-1/j}$ (i.e., $L_{i+1/i+2}$).

By simulation, a paraxylene purity of 99.88% and a paraxylene yield of 96.18% are obtained.

Method According to the Invention

The raffinate withdrawal line is situated downstream of the bypass line isolation valve (referred to more simply as "downstream of the bypass line valve").

The feed lines (feeding feedstock or desorbent), and the extract line are situated upstream of the isolation valve.

When a fluid (feedstock or desorbent) is injected at plate $P_i$, use is made of an injection line connected to the bypass line $L_{i/i+1}$. The isolation valve isolating the bypass line $L_{i/i+1}$ is then closed to ensure that the injected fluid does indeed flow towards the plate $P_i$.

When the extract is withdrawn at plate $P_i$, use is made of an injection line connected to the bypass line $L_{i/i+1}$. The isolation valve isolating the bypass line $L_{i/i+1}$ is then closed.

When the raffinate is withdrawn at plate $P_i$, use is made of a withdrawal line connected to the bypass line $L_{i-1/i}$. The isolation valve isolating the bypass line $L_{i-1/i}$ is then closed.

In order to gain a clear understanding of the configuration of the reference method, a description is given of the configuration of the method when the desorbent is injected at plate $P_1$. At that moment, the desorbent is injected via the bypass line $L_{1/2}$. The feedstock is then injected at plate $P_8$ via the bypass line $L_{8/9}$. The extract is withdrawn at plate $P_3$ via the bypass line $L_{3/4}$. The raffinate is withdrawn at plate $P_{11}$ via the bypass line $L_{10/11}$.

In the method according to the invention, zone 1 contains fewer than 3 beds. When the desorbent is injected at plate $P_i$ via the bypass line $L_{i/i+1}$, the extract is withdrawn at plate $P_j$ (i.e., $P_{i+2}$) via the bypass line $L_{j/j+1}$ (i.e., $L_{i+2/i+3}$).

By simulation, a paraxylene purity of 99.91% and a paraxylene yield of 96.53% are obtained.

Example 2

Consider an SMB unit made up of 12 beds, of length 1.3 m and of internal radius 3.5 m, with an injection of feedstock, an injection of desorbent (which may also be referred to as eluent or solvent), a withdrawal of extract and a withdrawal of raffinate.

The adsorbent used is a zeolite of type BaX, and the eluent is paradiethylbenzene. The temperature is 175° C., and the pressure is 15 bar.

The feedstock is made up of 23 wt % of paraxylene, of 22 wt % of orthoxylene, of 50 wt % of metaxylene, and of 5 wt % of ethylbenzene with respect to the total weight of the feedstock. The changeover period ST employed is 45 seconds.

The feedstock and desorbent injection liquid flow rates are as follows:
565 $m^3 \cdot h^{-1}$ for the feedstock;
710 $m^3 \cdot h^{-1}$ for the desorbent;
namely a solvent ratio S/F=1.3.

The beds are distributed in the 2/5/3/2 configuration, which means to say that the distribution of the beds is as follows:
2 beds in zone 1;
5 beds in zone 2;
3 beds in zone 3;
2 beds in zone 4.

The plates have two mixing chambers. The total volume $(V_i + V_{i+1} + VL_{i/i+1})$, where $VL_{i/i+1}$ is the volume of the bypass line from plate $P_i$ to plate $P_{i+1}$ and where $V_i$ is the volume of the distribution/extraction system for plate $P_i$, represents 3% of the volume of the bed comprised between plate $P_i$ and plate $P_{i+1}$.

The synchronism is set at 100% for all the open bypass lines.

Reference Method

The effluent (raffinate or extract) withdrawal lines are situated upstream of the bypass line isolation valve (referred to more simply as "upstream of the bypass line valve").

The feed lines (feeding feedstock or desorbent) are situated downstream of the isolation valve.

When a fluid (feedstock or desorbent) is injected at plate $P_i$, use is made of an injection line connected to the bypass line $L_{i-1/i}$. The isolation valve isolating the bypass line $L_{i-1/i}$ is then closed to ensure that the injected fluid does indeed flow towards the plate $P_i$.

When an effluent (extract or raffinate) is withdrawn at plate $P_i$, use is made of a withdrawal line connected to the bypass line $L_{i/i+1}$. The isolation valve isolating the bypass line $L_{i/i+1}$ is then closed.

In order to gain a clear understanding of the configuration of the reference method, a description is given of the configuration of the method when the desorbent is injected at plate $P_1$. At that moment, the desorbent is injected via the bypass line $L_{12/1}$. The feedstock is then injected at plate $P_8$ via the bypass line $L_{7/8}$. The extract is withdrawn at plate $P_3$ via the bypass line $L_{3/4}$. The raffinate is withdrawn at plate $P_{11}$ via the bypass line $L_{11/12}$.

In the reference method, zone 4 contains fewer than 3 beds. When the raffinate is withdrawn at plate $P_i$ via the bypass line $L_{i/i+1}$, the desorbent is injected at plate $P_j$ (i.e. $P_{i+2}$) via the bypass line $L_{j-1/j}$ (i.e. $L_{i+1/i+2}$).

By simulation, a paraxylene purity of 99.76% and a paraxylene yield of 96.95% are obtained.

Method According to the Invention

The effluent (raffinate or extract) withdrawal lines and the desorbent injection line are situated upstream of the bypass line isolation valve (referred to more simply as "upstream of the bypass line valve").

The feedstock feed line is situated downstream of the isolation valve.

When the desorbent is injected at plate $P_i$, use is made of an injection line connected to the bypass line $L_{i/i+1}$. The isolation valve isolating the bypass line $L_{i/i+1}$ is then closed to ensure that the injected fluid does indeed flow towards the plate $P_i$.

When the feedstock is injected at plate $P_i$, use is made of an injection line connected to the bypass line $L_{i-1/i}$. The isolation valve isolating the bypass line $L_{i-1/i}$ is then closed to ensure that the injected fluid does indeed flow towards the plate $P_i$.

When an effluent (extract or raffinate) is withdrawn at plate $P_i$, use is made of a withdrawal line connected to the bypass line $L_{i/i+1}$. The isolation valve isolating the bypass line $L_{i/i+1}$ is then closed.

In order to gain a clear understanding of the configuration of the reference method, a description is given of the configuration of the method when the desorbent is injected at plate $P_1$. At that moment, the desorbent is injected via the bypass line $L_{1/2}$. The feedstock is then injected at plate $P_8$ via the bypass line $L_{7/8}$. The extract is withdrawn at plate $P_3$ via the bypass line $L_{3/4}$. The raffinate is withdrawn at plate $P_{11}$ via the bypass line $L_{11/12}$.

In the method according to the invention, zone 4 contains fewer than 3 beds. When the raffinate is withdrawn at plate $P_i$ via the bypass line $L_{i/i+1}$, the desorbent is injected at plate $P_j$ (i.e. $P_{i+2}$) via the bypass line $L_{j/j+1}$ (i.e. $L_{i+2/i+3}$).

By simulation, a paraxylene purity of 99.81% and a paraxylene yield of 96.99% are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for the simulated moving bed separation of a feedstock (F) in a simulated moving bed separation device, the device comprising:
   at least one column comprising a plurality of beds of adsorbent ($A_i$) which are separated by plates ($P_i$) each comprising a distribution/extraction system; and
   external bypass lines ($L_{i/i+1}$) directly joining two successive plates ($P_i$, $P_{i+1}$), each external bypass line comprising fluid (F, D) feed points and effluent (E, R) withdrawal points,
   wherein said method comprises:
   the at least one column is fed with the feedstock (F) and a desorbent (D) and at least one extract (E) and at least one raffinate (R) is withdrawn from the at least one column, the feed and withdrawal points being shifted during the course of time by an amount corresponding to one adsorbent bed with a switchover period (ST) and determining a plurality of operating zones of the device, and notably the following main zones:
   a zone 1 for the desorption of the compounds from the extract, this zone being comprised between the feed for the desorbent (D) and the withdrawal of the extract (E),
   a zone 2 for the desorption of the compounds from the raffinate, this zone being comprised between the withdrawal of the extract (E) and the feed for the feedstock (F),
   a zone 3 for the adsorption of the compounds from the extract, this zone being comprised between the feed for the feedstock (F) and the withdrawal of the raffinate (R), and
   a zone 4 situated between the withdrawal of the raffinate (R) and the feed for the desorbent (D);
   in which method:
   at least one zone contains fewer than three beds,
   if the stream (D, E, F, R) delimiting said zone containing fewer than three beds (1, 2, 3, 4) and situated upstream of said zone (1, 2, 3, 4) is injected or withdrawn at the plate $P_i$ via the bypass line $L_{i/i+1}$, then the stream (E, F, R, D) delimiting the zone and situated downstream of said zone (1, 2, 3, 4) is injected/withdrawn at the plate $P_j$ via the bypass line $L_{j/j+1}$, and
   if the stream (E, F, R, D) delimiting said zone containing fewer than three beds (1, 2, 3, 4) and situated downstream of said zone (1, 2, 3, 4) is injected or withdrawn at the plate $P_i$ via the bypass line $L_{i-1/i}$, then the stream (D, E, F, R) delimiting the zone (1, 2, 3, 4) and situated upstream of said zone (1, 2, 3, 4) is injected/withdrawn at the plate $P_j$ via the bypass line $L_{j-1/j}$,
   the plate $P_i$ corresponding to one plate of the column,
   the plate $P_j$ corresponding to a plate other than $P_i$,
   the bypass line $J_{i-1/i}$ being the line joining the two successive plates $P_{i-1}$ and $P_i$,
   the bypass line $L_{i/i+1}$ being the line joining the two successive plates $P_i$ and $P_{i+1}$,
   the bypass line $L_{j-1/j}$ being the line joining the two successive plates $P_{j-1}$ and $P_j$,
   the bypass line $L_{j/j+1}$ being the line joining the two successive plates $P_j$ and $P_{j+1}$.

2. The method according to claim 1, in which:
   if zone 1 contains on average fewer than three beds, then when the desorbent (D) is injected on the plate $P_i$ via the bypass line $L_{i/i+1}$, the extract (E) is withdrawn on the plate $P_j$ via the bypass line $L_{j/j+1}$;
   if zone 2 contains on average fewer than three beds, then when the feedstock (F) is injected on the plate $P_i$ via the bypass line $L_{i-1/i}$, the extract (E) is withdrawn on the plate $P_j$ via the bypass line $L_{j-1/j}$;
   if zone 3 contains on average fewer than three beds, then when the feedstock (F) is injected on the plate $P_i$ via the bypass line $L_{i/i+1}$, the raffinate (R) is withdrawn on the plate $P_j$ via the bypass line $L_{j/j+1}$; and
   if zone 4 contains on average fewer than three beds, then when the desorbent (D) is injected on the plate $P_i$ via the bypass line $L_{i-1/i}$, the raffinate (R) is withdrawn on the plate $P_j$ via the bypass line $L_{j-1/j}$.

3. The method according to claim 1, in which:
   if zone 1 contains on average fewer than three beds, then when the extract (E) is withdrawn on the plate $P_i$ via the bypass line $L_{i-1/i}$, the desorbent (D) is injected on the plate $P_j$ via the bypass line $L_{j-1/j}$;
   if zone 2 contains on average fewer than three beds, then when the extract (E) is withdrawn on the plate $P_i$ via the bypass line $L_{i/i+1}$, the feedstock (F) is injected on the plate $P_j$ via the bypass line $L_{j/j+1}$;
   if zone 3 contains on average fewer than three beds, then when the raffinate (R) is withdrawn on the plate $P_i$ via the bypass line $L_{i-1/i}$, the feedstock (F) is injected on the plate $P_j$ via the bypass line $L_{j-1/j}$; and
   if zone 4 contains on average fewer than three beds, then when the raffinate (R) is withdrawn on the plate $P_i$ via the bypass line $L_{i/i+1}$, the desorbent (D) is injected on the plate $P_j$ via the bypass line $L_{j/j+1}$.

4. The method according to claim 1, in which the plate $P_i$ is connected to the bypass line $L_{i-1/i}$ and to the bypass line $L_{i/i+1}$.

5. The method according to claim 1, in which each plate ($P_i$) comprises a plurality of distribution-mixing-extraction panels of the parallel sectors type with asymmetric feed.

6. The method according to claim 1, in which the feedstock (F) contains paraxylene or metaxylene within a mixture of C8 aromatic hydrocarbons.

7. The method according to claim 1, in which the plurality of beds of adsorbent ($A_i$) is distributed between zones 1 to 4 in a configuration referred to as being of type a/b/c/d, wherein the distribution of the beds is as follows:
   a is the mean number of beds in zone 1;
   b is the mean number of beds in zone 2;
   c is the mean number of beds in zone 3;
   d is the mean number of beds in zone 4;
   $a=(n*0.208)*(1\pm0.2)$;
   $b=(n*0.375)*(1\pm0.2)$;
   $c=(n*0.292)*(1\pm0.2)$; and
   $d=(n*0.125)*(1\pm0.2)$.

8. The method according to claim 1, in which the plurality of beds of adsorbent ($A_i$) is distributed between zones 1 to 4 in a configuration referred to as being of type a/b/c/d, wherein the distribution of the beds is as follows:
   a is the mean number of beds in zone 1;
   b is the mean number of beds in zone 2;
   c is the mean number of beds in zone 3;
   d is the mean number of beds in zone 4;
   a=2;
   b=5;
   c=3; and
   d=2.

9. The method according to claim 1, in which the column comprises n beds of adsorbent ($A_i$), n being a natural whole number comprised between 6 and 15.

10. The method according to claim 1, in which the column comprises n beds of adsorbent ($A_i$), n being a natural whole number comprised between 8 and 12.

11. The method according to claim 1, in which the switchover period (ST) is between 20 seconds and 120 seconds.

12. The method according to claim 1, in which the switchover period (ST) is between 40 seconds and 100 seconds.

13. The method according to claim 1, in which the feedstock is a mixture containing at least 95% C8 aromatic compounds.

14. The method according to claim 1, in which the feedstock is a mixture containing at least 97% C8 aromatic compounds.

15. The method according to claim 6, in which the feedstock (F) contains at least 15 wt% of paraxylene with respect to the total weight of the feedstock.

16. The method according to claim 6, in which the feedstock (F) contains at least 30 wt% of metaxylene with respect to the total weight of the feedstock.

17. The method according to claim 15, in which the feedstock (F) contains at least 30 wt% of metaxylene with respect to the total weight of the feedstock.

18. The method according to claim 1, in which the column is operate at a temperature of between 120° C. and 190° C.

19. The method according to claim 1, in which the column is operate at a pressure of between 0.3 MPa and 3 MPa.

20. The method according to claim 18, in which the column is operate at a pressure of between 0.3 MPa and 3 MPa.

\* \* \* \* \*